United States Patent [19]

Hix

[11] 4,137,909
[45] Feb. 6, 1979

[54] MEDICAL ELECTRODE

[75] Inventor: Ernet T. Hix, Dayton, Ohio

[73] Assignee: NDM Corporation, Dayton, Ohio

[21] Appl. No.: 820,838

[22] Filed: Aug. 1, 1977

[51] Int. Cl.² .............................................. A61B 5/04
[52] U.S. Cl. ............................ 128/2.06 E; 128/2.1 E;
128/417; 128/DIG. 4
[58] Field of Search ............... 128/2.06 E, 2.1 R, 404,
128/410, 411, 416–418, DIG. 4

[56] References Cited

U.S. PATENT DOCUMENTS

| 3,078,850 | 2/1963  | Schein et al. ............... 128/2.1 E X |
| 3,187,745 | 6/1965  | Baum et al. ................. 128/2.06 E  |
| 3,534,733 | 10/1970 | Phipps et al. ............... 128/2.1 E   |
| 3,701,346 | 10/1972 | Patrick, Jr. et al. ......... 128/2.06 E  |
| 3,795,241 | 3/1974  | Golovko ..................... 128/2.06 E  |
| 3,805,769 | 4/1974  | Sessions .................... 128/2.06 E  |
| 3,982,529 | 9/1976  | Sato ......................... 128/2.06 E  |

FOREIGN PATENT DOCUMENTS

| 2152808 | 4/1973 | Fed. Rep. of Germany ...... 128/2.06 E |
| 2208653 | 4/1973 | Fed. Rep. of Germany ...... 128/2.06 E |
| 2548805 | 5/1977 | Fed. Rep. of Germany ...... 128/2.06 E |

Primary Examiner—Lee S. Cohen
Attorney, Agent, or Firm—Dybvig & Dybvig

[57] ABSTRACT

A medical electrode for attachment to the skin of a patient has a cup member forming a cavity for containing an electroylyte. The cup member has a base portion which is movable inwardly of the cup member so as to contract the interior volume of the cavity and in so doing displace the electrolyte outwardly of the cup member for contact to the skin of a patient. In a modification, the configuration of the base of the cup member allows an electrode conductor to be supported out of contact with the electroylyte until the base portion is moved to displace electrolyte outwardly of the cup member.

6 Claims, 4 Drawing Figures

MEDICAL ELECTRODE

BACKGROUND OF THE INVENTION

1. Field of the Invention

This invention relates to medical electrodes for use in contact with the skin of a patient and to means included in the electrode construction for transferring a skin-contacting electrolyte sponge between storage and usage positions.

2. Prior Art

U.S. Pat. No. 3,701,346 illustrates a medical electrode housing an oversized electrolyte sponge protected by a removable cover. To prevent squeezing of electrolyte from the sponge, the protective cover has an oversized cavity which receives the sponge without premature squeezing of the sponge during assembly and storage. Following removal of the protective cover, the electrolyte sponge is exposed to the pressure of the patient's skin, which squeezes the sponge, thus assuring a liberal wetting of the patient's skin with electrolyte from the sponge. U.S. Pat. Nos. 3,805,769 and 3,982,529 illustrate other techniques for providing electrolyte at the skin surface when the electrode is in use.

An object of the present invention is to provide a new and improved medical electrode and, more particularly, a medical electrode having a cup which is actuable so as to transfer electrolyte means from a storage position within the cup to an outwardly displaced position for effective contact with the skin.

SUMMARY OF THE INVENTION

In the present invention, an electrode cup for receipt of electrolyte means such as an electrolyte-soaked sponge is formed with a base actuable from a first position in which the base forms an outer wall of the cup to a second position in which the base is depressed inwardly of the cup, the actuation of the base from the first position to the second position requiring a manual effort and displacing the electrolyte sponge outwardly from a storage chamber of the cup so as to produce firm contact between the electrolyte sponge and the skin of a patient. In a modification, a conductor attached to the base of the electrode cup is initially supported remotely from the electrolyte means within the cup so as to prevent contact between electrolyte and the conductor until after the base portion has been actuated to press the electrolyte means against the skin of a patient and to press the conductor into firm engagement with the electrolyte.

DESCRIPTION OF THE PREFERRED EMBODIMENT

Figure 1:
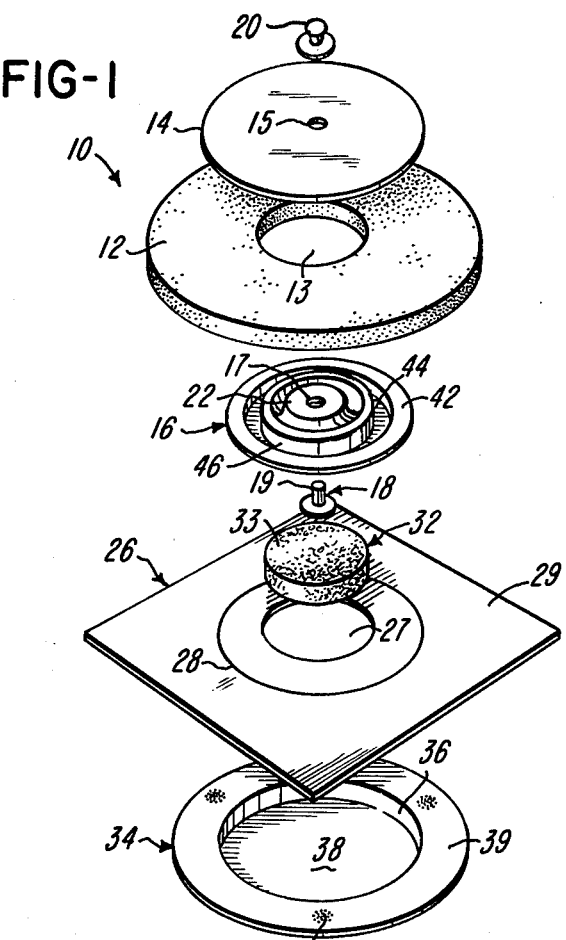
FIG. 1 is an exploded perspective view illustrating a medical electrode in accordance with the present invention.

Referring to FIG. 1, the drawings illustrate a medical electrode 10 in which an annulus of elastic foam sponge material 12 has a central aperture 13 for receiving the closed end of a cup member 16. A circlet 14 of a flexible plastic material, such as a vinyl plastic, secured by adhesive 23 lies over the closed end of the cup member 16 and closes the aperture 13 in the foam sponge 12.

The members 12, 14 and 16 are secured in assembled relation by means of a two-part snap fastener comprising a male part 18 within the cup member 16 and a female part 20 into which the male part 18 has been pressed in conventional fashion, the male part having an eyelet or stem 19 passing through an aperture 17 located in the base 22 of the cup member 16 and an aperture 15 located in the center of the circlet 14.

The cup member 16 houses an electrolyte sponge 32, which is preferably an open cell foam plastic and which is saturated prior to assembly of the electrode with an electrolyte 33.

Figure 2:
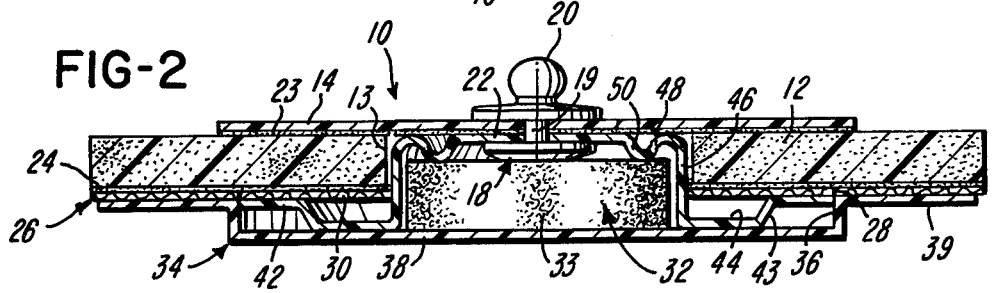
FIG. 2 is a transverse section view of the assembled electrode.

The foam sponge annulus 12 has adhesive 24 applied to its lower surface, as appears in FIG. 2, and such adhesive is protected during storage and shipment by a layer of release paper 26. The release paper 26 has a central opening 27 of the same size as the aforementioned opening 13 to receive the closed end of the cup member 16.

The release paper 26 also has an incision 28, whose diameter corresponds to the outside diameter of a flange 42 projecting outwardly from the cup member 16. As best appears in FIG. 2, the release paper 26 has an included annulus 30 which becomes trapped between the flange 42 of the cup member 16 and the sponge annulus 12. Beyond the diameter of the annulus 30, the release paper 26 extends outwardly in the form of a square sheet whose corners 29 project beyond the outside diameter of the sponge annulus 12.

The electrolyte 33 residing in the sponge 32 is protected from dust and from a premature compression of the sponge, such as would extrude electrolyte from the sponge, by means of a protective cover 34 having an integral annular wall 36 which supports a panel 38 recessed into the cover 34 so as to accommodate the shape of the cup member 16. Thus, as appears in FIG. 2, the wall 36 receives the outside margin of the aforementioned flange 42, and the cover 34 is provided with an outwardly projecting flange 39 affixed to the release paper 26 outside the incision 28 by adhesive tacks 40, such as appear in FIG. 1.

The arrangement is such that the protective cover 34 can protect the sponge 32 from damage until immediately prior to the use of the electrode, whereupon the corners 29 of the release paper 26 can be pulled away from the adhesive surface of the sponge annulus 12. As the outer margin of the release paper is pulled away from the sponge annulus 12, it carries with it the adhesively tacked protective cover 34. However, due to the presence of the aforementioned incision 28, the included annulus 30 remains in adhesive contact with the sponge annulus 12 because it is trapped between the outer flange 42 of the cup member 16 and the sponge annulus 12.

Referring in greater detail to the cup member 16, it can be noted that the cup member includes an annular wall 46 supported inwardly of the aforementioned flange 42 by means of a wall portion 43 forming a channel 44.

The wall 46 joins to the base 22 by means of a first arch 48 curving downwardly or forwardly toward the mouth of the cup member. The first arch 48 is followed by a second arch 50 curving upwardly or rearwardly and then radially inwardly to integrally merge with the base 22. The arches 48 and 50 encircle the male snap fastener part 18.

When the snap fastener is pressed downwardly, as it appears in FIG. 2, the arch 50 opens as the arch 48 closes to permit the base 22 to drop downwardly to a new position disposed deeply within the annular wall 46. This downward movement reverses the curvature of the arch 50, and the inward bias of the arch 48 resists an upward return of the base 22.

Figure 3:
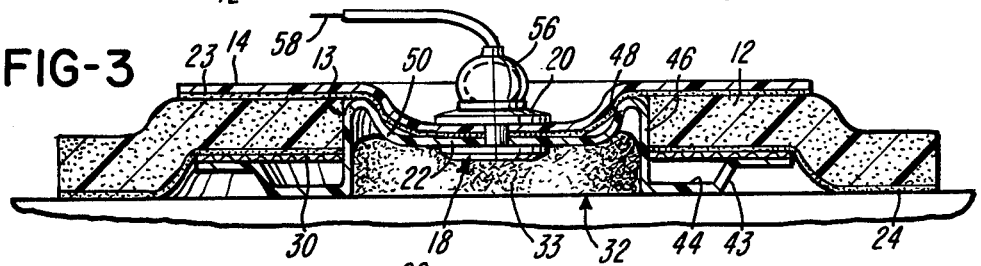
FIG. 3 is a section view analogous to that of FIG. 2, illustrating the electrode after actuation for contact of electrolyte to the skin of a patient.

The nature of the reversal that occurs in the arch 50 can be better visualized after a comparison of FIG. 2, which shows the electrode assembly before the female snap fastener 20 has been manually pressed downwardly, and FIG. 3, which shows the approximate cross sectional appearance of the cup member 16 after the female snap fastener 20 has been pressed downwardly a sufficient distance to effect a reversal of the arch 50.

A further comparison of FIGS. 2 and 3 will show that the axial dimension of the wall 46 of the cup 16 was sized to accommodate the axial dimension of the electrolyte sponge 32 without compressing that sponge. However, when the female snap fastener member 20 is pressed downwardly to effect the transition illustrated in FIG. 3, the interior volume of the cup member 16 is shrunk substantially with the result that the male snap fastener part 18 presses firmly against the sponge 32 and presses that sponge firmly against the patient's skin, as schematically illustrated in FIG. 3.

As is common in the use of medical electrodes such as described, the female snap fastener 20 is engaged by a detachable fastener 56 having a conductor 58 extending therefrom for the purpose of conducting electrical signals from the skin of the patient to appropriate electrocardiograph equipment. As will be apparent to those skilled in the art, attachment of the fastener 56 to the female snap fastener 20 may be accomplished before actuation of the base of the electrode cup downwardly toward the skin, at the same time, or at a later time, depending upon the desires of the technician who applies the electrodes.

It is known that many electrode materials, such as the metal silver, undergo chemical reactions with the electrolyte, particularly when first contacted to the electrolyte. For this reason, electrodes which are prefilled with electrolyte have become popular. The prefilling necessitates that the electrode material will have been in contact with the electrolyte for substantial periods of time before applied to the skin of a patient. During such periods of time, the silver is thought to be passivated with respect to the electrolyte; and, by the time the electrode is contacted to the skin of the patient, passivation will be complete so that signal noises attributable to reactions occurring between the electrolyte and the conductor material are minimized.

Other metals, particularly zinc, are readily soluble as ions in an appropriately selected electrolyte, such as silver chloride, and require no passivation. In and of itself, this is an advantageous feature. However, in the case of prefilled electrodes, the continuing dissociation or ionization of the zinc or other readily soluble metal contacted by the electrolyte necessitates that the electrode conductor include a sufficient amount of the zinc or other metal so as not to be fully ionized during storage of the electrode.

Alternatively, it is desirable that the zinc or other readily soluble conductive material be stored out of contact with the electrolyte and permitted to contact the electrolyte only immediately before the electrode is to be used. This enables construction of electrodes having only minimal amounts of a conductor material which can be readily soluble when contacted by the electrolyte.

Figure 4:
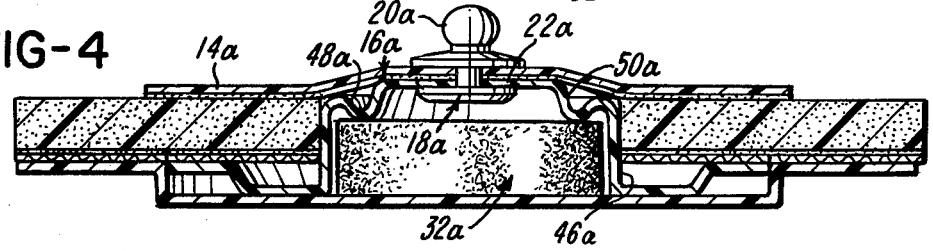
FIG. 4 is a section view analogous to FIG. 2, illustrating a modification.

In the modification illustrated in FIG. 4, structural features substantially the same as previously described in reference to the preferred embodiment have been identified with the same reference numbers as employed in discussing the preferred embodiment, the suffix "a" being used in association with the reference numbers to distinguish the structural features of the modification from those of the preferred embodiment.

As was true of the preferred embodiment, the cup 16a of the modification includes an annular wall 46a supporting a base 22a. The base 22a is surrounded by a downwardly curved arch 50a followed outwardly by an upwardly directed arch 48a.

In marked departure from the preferred embodiment, the arches 48a and 50a are so sized relative to the snap fastener part 18a and the electrolyte sponge 32a that the sponge 32a will not contact the fastener part 18a during storage of the electrode assembly.

Except for the foregoing difference, the modification of FIG. 4 may be constructed and assembled in the same manner as has been described in reference to the preferred embodiment.

The actuation of the modification is essentially as has been described in connection with the preferred embodiment. Thus, by exerting a downward pressure on the snap fastener part 20a, the part 18a, which is initially out of contact with the electrolyte sponge 32a, is pushed downwardly into the cup 16a, causing the snap fastener part 18a to engage the electrolyte sponge 32a as that sponge is advanced outwardly of the cup 16a and pressed against the skin of a patient.

This modification offers the advantage that the snap fastener part 18a may be a relatively soluble metal, such as zinc, or may be a composite plastic material including zinc or the like. Prior to use of the modification, the arch 50a operates to maintain a separation between the male snap fastener part 18a and the electrolyte sponge 32a. This protects the readily soluble metal comprising the snap fastener part 18a from a premature dissolution into the electrolyte of the sponge 32a. Prior to the time electrocardiograph traces are to be taken, the snap fastener part 20a is actuated downwardly to cause the snap fastener part 18a to contact the electrolyte of the sponge 32a.

It will be noted that both of the cup members 16 and 16a disclosed in the present application are of a relatively low profile configuration. The present invention offers the advantage, however, that, in each of the two cup configurations described, the snap fastener part 20, which initially protrudes upwardly from the base of the cup, is pressed into the cup upon actuation of the snap fastener to transfer the electrolyte sponge from within the cup to an outwardly extended position bearing against the skin of the patient, thus further reducing the electrode profile. A variety of materials may be used to form the cup members 16 and 16a, examples being vinyl plastic, linear polyethylene and cellulose acetate butyrate.

Although the preferred embodiments of the present invention have been described, it will be understood that various changes may be made within the scope of the appended claims.

Having thus described my invention, I claim:

1. In a medical electrode of the type adapted to be adhered to the skin, said electrode having means defining a cavity receiving an electrolyte and having an opening adapted to open to the skin, and having conductive means at the base of said cavity for allowing external connection to said electrolyte, the improvement wherein said means defining a cavity comprises a wall surrounding said base and said electrolyte and means supporting said base and said conductive means in a first position rearward with respect to said wall for an expanded volume of said cavity and for movement to a second position inwardly of said wall to reduce the volume of said cavity and thus press said electrolyte outwardly of said cavity through said opening for engagement with and compression against the skin, said means supporting said base resisting return of said base from said second position to said first position.

2. The improvement of claim 1 wherein said means supporting said base comprises a first arch portion integrally attached to said surrounding wall and arching inwardly of said cavity and a second arch portion arching rearwardly of said cavity from said first arch portion and integrally joined to said base, the direction in which said second arch portion arches reversing upon movement of said base toward said second position, said reversing of the direction in which said second arch portion arches causing said second arch portion to resist a return of said base to said first position.

3. The improvement of claim 2 wherein said first and second arch portions cooperate to support said electrolyte remotely from said conductive means in said first position.

4. The improvement of claim 1 wherein said means supporting said base and said conductive means in a first position supports said conductive means remotely from said electrolyte and, in said second position, supports said conductive means in contact with said electrolyte.

5. The improvement of claim 1 wherein said base, said surrounding wall and said means supporting said base are integrally formed, and said conductive means passes through said base.

6. In a medical electrode of the type adapted to be adhered to the skin, said electrode having means defining a cavity receiving an electrolyte and having an opening adapted to open to the skin, and having conductive means affixed to the base of said cavity for allowing external connection to said electrolyte, the improvement wherein said means defining a cavity comprises a wall surrounding said base and said electrolyte, and means joined to said wall and to said base for supporting said base in a first position remote from said skin and, upon application of a pressure to said base, shifting said base to a second position closer to said skin to reduce the volume of said cavity and thus press said electrolyte through said opening against the skin, and means joined to said wall and to said base having a curvature which reverses upon movement of said base from said first position to said second position so that said means joined to said wall and to said base resists return of said base from said second position to said first position.

* * * * *

UNITED STATES PATENT AND TRADEMARK OFFICE
CERTIFICATE OF CORRECTION

PATENT NO. : 4,137,909
DATED : February 6, 1979
INVENTOR(S) : Ernest T. Hix

It is certified that error appears in the above-identified patent and that said Letters Patent are hereby corrected as shown below:

In the bibliographic data, code [75], "Ernet" should be
---Ernest---

In the Abstract, code [57], line 3, "electroylyte" should be ---electrolyte---

In the Claims, Claim 6, column 6, line 25, "and" should be ---said---

Signed and Sealed this

First Day of May 1979

[SEAL]

Attest:

RUTH C. MASON
*Attesting Officer*

DONALD W. BANNER
*Commissioner of Patents and Trademarks*